United States Patent
Gebhardt et al.

(10) Patent No.: US 7,687,632 B2
(45) Date of Patent: *Mar. 30, 2010

(54) PROCESS FOR THE PREPARATION OF PYRIDINE DERIVATIVES

(75) Inventors: Joachim Gebhardt, Wachenheim (DE); Norbert Götz, Worms (DE); Hagen Jaedicke, Ludwigshafen (DE); Guido Mayer, Gönnheim (DE); Michael Rack, Heidelberg (DE)

(73) Assignee: Dow AgroSciences LLC, Indianapolis, IN (US)

( * ) Notice: Subject to any disclaimer, the term of this patent is extended or adjusted under 35 U.S.C. 154(b) by 470 days.

This patent is subject to a terminal disclaimer.

(21) Appl. No.: 10/584,354

(22) PCT Filed: Dec. 22, 2004

(86) PCT No.: PCT/EP2004/014590

§ 371 (c)(1),
(2), (4) Date: Jun. 4, 2007

(87) PCT Pub. No.: WO2005/063780

PCT Pub. Date: Jul. 14, 2005

(65) Prior Publication Data

US 2007/0249837 A1    Oct. 25, 2007

(30) Foreign Application Priority Data

Dec. 23, 2003 (EP) .................... 03029730

(51) Int. Cl.
*C07D 211/72* (2006.01)
*C07F 9/02* (2006.01)

(52) U.S. Cl. ........................ 546/290; 568/15

(58) Field of Classification Search ............... 546/290; 568/15

See application file for complete search history.

(56) References Cited

U.S. PATENT DOCUMENTS

| 3,993,656 | A | 11/1976 | Rooney et al. |
| 6,130,335 | A | 10/2000 | Johnson et al. |
| 7,488,828 | B2 * | 2/2009 | Hamilton et al. ............ 546/290 |

OTHER PUBLICATIONS

Jones, Reuben G. et al; "Pyridine Synthesis. III. Preparation and Reactions of Some Penta-substituted Pyridines", Journal of the American Chemical Society, 1951, pp. 5610-5614, vol. 73 No. 12.
Knoevenagel, E. et al: "Synthesen in der Pyridinrethe. Ueber die Einwirkung von Malonester und Malonamid auf Aminoacetylacelon," Chem. Berichte, 1902, pp. 2390-2396.

* cited by examiner

*Primary Examiner*—D. Margaret Seaman
*Assistant Examiner*—Nizal S Chandrakumar
(74) *Attorney, Agent, or Firm*—Craig E. Mixan

(57) ABSTRACT

Process for the preparation of substituted pyridine derivatives of formula (I) comprising reaction of a α-β-unsaturated carbonyl compound of formula (II) $R^3$—C(O)—C($R^1$)=C($R^2$)-G with a Wittig reagent or Horner-Wadsworth-Emmons reagent in the presence of a base and optionally subsequent cyclization.

(I)

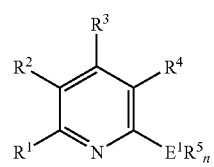

4 Claims, No Drawings

PROCESS FOR THE PREPARATION OF PYRIDINE DERIVATIVES

Substituted pyridines are valuable building blocks in organic systems such as pharmaceutical or agrochemical synthesis, e.g. herbicide, fungicide or insecticide synthesis.

Although there are known synthesis routes to substituted pyridine derivates in the literature (cf synthesis of 4-trifluoromethyl substituted pyridine via Reformatsky route: Jiang et al. Organic Process Research & Development 2001, Vol. 5, 531-534); synthesis of 6-trifluoromethyl substituted pyridines: EP 1 340 747 A (Bayer A G), E. Okada et al., Heterocycles, 46, 129-132 (1997), P. J. De Fraine et al., GB 2,305,174; Y. Yakunin Chem. Heterocycl. Comp. 2000, 36 (12), 1431-1436; JP 2001158774 (Ishihara Sangyo Kaisha)) there remains need for versatile synthesis routes yielding pyridine derivates having an electron withdrawing substituent in the 4-position of the pyridine ring. Usually the synthesis for pyridine derivatives with this electron withdrawing substituents (e.g. trifluoromethyl) yields the 6-substituted pyridine instead of 4-substituted pyridine.

Electron withdrawing substituent shall mean herein a substituent having a -M (resonance or mesomeric) and/or a -I (inductive) effect; preferably such substituents are a) $C_1$-$C_{20}$carbo organic radicals, preferably $C_{1-20}$-alky or $C_{6-20}$aryl substituents—which bear at least one halogen (F, Cl, Br, I) atom or are fully halogenated, which means all non-C—C-bonds are C-halogen bonds. Preferably the halogens are chlorine or fluorine, most preferably fluorine. Very preferable are fully fluorinated $C_{1-6}$-alkyls or $C_{6-10}$-aryls, such as trifluormethyl, pentafluorethyl, heptafluorpropyl, heptafluorisopropyl, pentafluorphenyl, most preferably trifluormethyl;

b) $C_{1-20}$alkoxy or $C_{6-20}$-aryloxy both bearing at least one halogen atom (F, Cl, Br, I) or which are fully halogenated (cf above), preferably the halogen atoms are chlorine or fluorine. Very preferable are fully fluorinated $C_{1-6}$-alkoxy or $C_{6-10}$-aryloxy, such as trifluormethoxy, pentafluorphenoxy;

c) cyano;

d) nitro.

A further demand is for pyridine derivatives which bear in the 3-position a sulfur containing group which sulfur is bound directly to the pyridine ring.

A further demand is for pyridine derivatives which bear in the 4-position an electron withdrawing group and in the 3-position a sulfur containing group which sulfur is directly bound to the pyridine ring.

Another demand is for pyridine derivatives which bear in the 2-position a hydroxy, amino or alkoxy substituent and preferably additionally in the 4-position an electron withdrawing group.

Another demand is for pyridine derivatives which bear in the 2-position a hydroxy, amino or alkoxy substituent and preferably additionally in the 4-position an electron withdrawing group and in the 3-position a sulfur containing group which sulfur is directly bound to the pyridine ring.

The object of the present invention is to provide a versatile process for the preparation of substituted pyridines, in particular substituted pyridines which have an electron withdrawing substituent in the 4-position or pyridines which bear in the 4-position an electron withdrawing group and in the 3-position a sulfur containing group which sulfur is directly bound to the pyridine ring.

The further object the present invention is to provide phosphorus compounds and/or other intermediates which are useful in the preparation of above mentioned pyridine synthesis process.

The further object the present invention is to provide the use of phosphorus compounds, α-β-unsaturated carbonyl compound and/or other intermediates in the preparation of substituted pyridine synthesis.

Therefore the process as defined in the claims as well as the phosphorus compounds and/or other intermediates, as well as their respective use in synthesis of pyridine derivatives have been found.

Usually the phosphorus reagents (III) are prepared by reaction of a phosphorus compound $P(Ar)_3$—in which Ar is a substituted or preferably unsubstituted $C_{6-20}$aryl, such as phenyl, tolyl, naphtyl.- or $P(OR')_3$—in which R' is equal or different and independently means $C_{1-20}$alkyl, branched or straight or cyclic, such as methyl, ethyl, n-propyl, i-propyl, n-butyl or $C_{6-20}$aryl, such as phenyl, tolyl, benzyl, with a suitable organic halide of formula a III.

Hal—C($E_nR^6{}_m$)H—Y     (a III)

wherein $E_nR^6{}_m$=in which if n=m=1 than E=S and $R^6$=$C_{1-20}$-alkyl (branched or straight chain or cyclic); $C_{6-20}$-aryl—which each of those may be substituted with one or more of the following groups:

F, Cl, Br, I, $C_{1-20}$-alkoxy, $C_{6-20}$-aryloxy, non substituted or preferably substituted amino; F, Cl, Br, I;

if n=0 and m=1 than $R^6$=H, $C_{1-20}$-alkyl (branched or straight chain or cyclic); $C_{6-20}$-aryl —which each of those may be substituted with one or more of the following groups:

F, Cl, Br, I, $C_{1-20}$-alkoxy, $C_{6-20}$-aryloxy, non substituted or preferably substituted amino; F, Cl, Br, I;

Hal=F, Cl, Br, I;

Y=—CN; —C(O)NH$_2$; —C(O)OCR$^7$ with R$^7$=as defined for R1 below, except H;

in a know manner yielding the phosphonium salt [(Ar)$_3$P-C ($E_nR^6{}_m$)H-Y]$^+$Hal$^-$ in which the variables have the same meaning as under aII above ("Wittig Precursor" as follows) or (O)P(OR')$_2$—C($E_nR^6{}_m$)H-Y in which the variables have the same meaning as under all above ("Horner Precursor" as follows). Those reactions are generally known.

Reaction Path A (Wittig Reagent or Horner Reagent Plus α-β Unsaturated Carbonyl Compound Which is 4-amino Substituted)

Path A 1

1. The Wittig Precursor in which $E_nR^6{}_m$ has the meaning n=m=1; E=S and $R^6$ has the meaning as defined above and further in which Y is —CN or —C(O)OR7 (R7 as defined above), may be as generally known reacted with a base, such as alcoholates, hydrides, carbonates or organo-lithium-compounds preferably organolithium compounds such as n-butyl lithium yielding the Wittig Reagent (IIIa1);

the Horner Precursor in which $E_nR^6{}_m$ has the meaning n=m=1; E=S and $R^6$ has the meaning as defined above and further in which Y is —CN or —C(O)OR7 (R7 as defined above), may be as generally known reacted with a base, such as alcoholates, hydrides, carbonates or organo-lithium-compounds preferably alkaline metal (Li, Na, K, Rb, Cs) alcoholates (very preferably in the presence of lithium salts, e.g. lithium halides), such as lithium alcoholates for example lithium ethoxide or lithium methoxide compounds yielding the Horner Reagent (IIIa2), which formally is bearing a carbanion

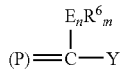 (IIIa)

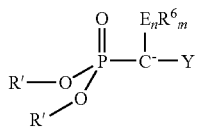 (IIIa2)

in which E=S and n and m=1, (P) is P(Ar)$_3$ (for IIIa) R' as defined above and Y=—CN, —C(O)OR$^7$ (R$^7$ as defined above), R$^6$ is defined as R$^1$, except H. Preferably R$^6$ is methyl, ethyl, propyl, isopropyl, benzyl or phenyl.

The abovementioned reactions can be conducted in the presence or in the absence of the below defined α-β- unsaturated carbonyl compound of formula (IIa).

2.) The Wittig Reagent (IIIa1) or Horner Reagent (IIIa2) is than reacted, as generally known in an organic solvent, such as alcohols (preferably for Horner Reagent), halogenated hydrocarbons or polar aprotic solvents (preferably for Wittig Reagents) like THF, DMF or NMP usually at a temperature in the range of from −15° C., to 120° C., preferably 0° C. to 70° C., with the α-β-unsaturated carbonyl compound of formula (IIa)

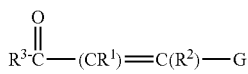 IIa wherein
R$^1$, R$^2$ independently the same or different are H; C$_{1-20}$-alkyl (branched or straight chain or cyclic); C$_{6-20}$-aryl—which each of those may be substituted with one or more of the following groups: F, Cl, Br, I, C$_{1-20}$-alkoxy, C$_{6-20}$-aryloxy, non substituted or preferably substituted amino-; F, Cl, Br, I, preferably R$^1$, R$^2$, are H, methyl, in particular H.
R$^3$ is the same as R$^1$ or R$^2$ (except H and halogens) and additionally R$^3$ shall mean —CN, —NO$_2$,. Preferably R$^3$ is an electron withdrawing group (as defined above) more preferably a fully fluorinated C$_{1-6}$alkyl (branched or straight) or fully fluorinated C$_{6-10}$-aryl, such as trifluoromethyl, pentafluoroethyl, heptafluoropropyl heptafluoroisopropyl, pentafluorophenyl, most preferably trifluoromethyl.
G=—NH$_2$ A very suitable compound IIa is F$_3$C—C(O)—CH=CH—NH$_2$.

The molar ratio of (IIIa1) or (IIIa2) to (IIa) is in general 1:1 to 1:3, preferably 1:1,2.

Path A1-1

This reaction leads, after neutralisation and extractive workup if Y=—CN (IIIa-1) to the respective pyridine derivatives, preferably—in case E=S—to the pyridine compounds (Ia-1)

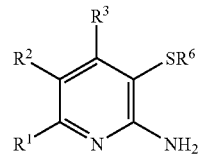 (Ia-1)

in which the variables, including their preferred meanings, are as defined above.

Preferred compounds of formula (Ia-1) are the ones in which R$^1$=H, Alkyl, R$^2$=H, Alkyl, R$^3$=—CF$_3$, —C$_2$F$_5$, n-C$_3$F$_7$, i-C$_3$F$_7$, R$^6$=methyl, benzyl in particular compound (I-a1) in which R$^1$, R$^2$=H, R$^3$=—CF$_3$, R$^6$=Me, benzyl.

Path A1-2

This reaction leads after hydrolytic workup under acidifying conditions with subsequent extraction if

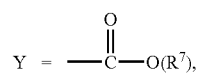 (IIIa-2)

(IIIa-2: R$^7$ as defined above, for example methyl, ethyl, n-propyl, i-propyl, n-butyl, i-butyl, tert.-butyl, sec-butyl, benzyl, phenyl) to the respective pyridine derivatives, preferably—in case E=S—to compounds Ia-2

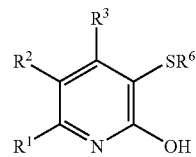 (Ia-2)

in which the variables, including their preferred meanings, are defined as above (e.g. under section "Path A1-1").

Particularly preferred are compounds Ia-2 in which R$^1$=R$^2$=H, R$^3$=—CF$_3$ and R$^6$=Me, benzyl.

Path A 2

The Wittig Reagent (IIIa1) or Horner Reagent (IIIa2)—in which the variables in the group E$_n$R$^6_m$ have the meaning n=0 and m=1, R$^6$=H, C$_{1-20}$-alkyl (branched or straight chain or cyclic); C$_{6-20}$-aryl—which each of those may be substituted with one or more of the following groups: F, Cl, Br, I, C$_{1-20}$-alkoxy, C$_{6-20}$-aryloxy, non substituted or preferably substituted amino; F, Cl, Br, I, preferably R$^6$=H, Alkyl—is reacted under the conditions as described under A1 2.) above with the α-β-unsaturated carbonyl compound (IIa) wherein the variables of IIa, including the preferred variables, are as defined under A1 2.) above.

The molar ratio of (IIIa1) or (IIIa2) to (IIa) is in general 1:1 to 1:3, preferably 1:1,2.

This reaction leads, depending on the meaning of variable Y in the Wittig Reagent or Horner reagent, to different pyridine derivatives.

A 2-1

Analogous to A1-1—if Y=—CN—the reaction yields the respective pyridine derivatives, preferably—if $E_nR^6_m$ has the meaning n=0 and m=1, $R^6$=H—the pyridine compounds Ia-3

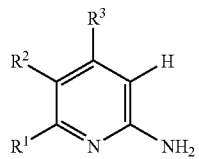
(Ia-3)

in which the variables, including their preferred meanings, are defined as above (e.g. under A1-2, A1-1).

Particularly preferred compounds Ia-3 are those in which $R^1=R^2$=H, $R^3$=—CF$_3$, —C$_2$F$_5$, —C$_3$F$_7$.

A2-2

Analogous to A1-2—if Y=—C(O)R$^7$ (R$^7$ as defined above, e.g. under A1-2)—the reaction yields the respective pyridine derivatives, preferably—if $E_nR^6_m$ has the meaning n=0 and m=1, $R^6$=H—the pyridine compounds Ia-4

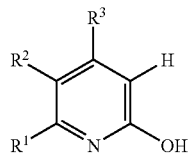
(Ia-4)

in which the variables, including their preferred meanings, are as defined above (e.g. under A1-2).

Particulary preferred compounds (Ia-4) are those in which $R^1=R^2$=H, $R^3$=—CF$_3$, —C$_2$F$_5$, —C$_3$F$_7$.

Reaction Path B (Phosphorus Agent Plus α-β-unsaturated Carbonyl Compound Which is Substituted in 4-position with a Leaving Group)

B1

1. The Wittig Precursor or Horner Precursor in which Y=—CN, —C(O)OR$^7$ or —C(O)NH$_2$ are reacted with base analogous to A1 1.)
   yielding the ylide reagent (IIIb1) and (IIIb2)

(IIIb1)

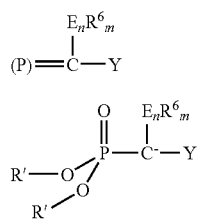

(IIIb2)

in which the variables have the same meaning as defined under A1 1.) above, except for Y which is —CN or —C(O)NH$_2$, or —C(O)OR$^7$.

2.) Reagent IIIb1 or IIIb2 can be then reacted analogous to A1 2.) above with the α-β-unsaturated carbonyl compound of formula IIb

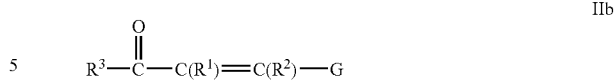
(IIb)

in which the variables, including their preferred meaning, have the same meaning as under A1 2.) above, except for G which is a leaving group.

Suitable leaving groups G are —OR$^1$, —NHR$^1$, —N(R$^1$)$_2$, halogen (F, Cl, Br, I) in which R$^1$ has the same meaning, including its preferred meaning, as specified for formula (II a) above, except H. Preferably R$^1$, independently the same or different, is a C$_{1-6}$alkyl such as methyl, ethyl, n-propyl, i-propyl, n-butyl, sec-butyl, tert.-butyl, cyclohexyl; i-butyl; a C$_{6-10}$aryl such as phenyl, tolyl, benzyl.

A very suitable compound IIb is F$_3$C—C(O)—CH=CH—OEt.

This reaction usually leads to a mixture of intermediates IV, see below.

B2

The Wittig Reagent or Horner Reagent in which Y=—CN or —C(O)NH$_2$ or —C(O)OR$^7$, are reacted analogous A 1 2.) above with the α-β-unsaturated carbonyl compound of formula II b defined under B 1 2.) above.

This reaction usually leads to a mixture of intermediates IVa, see below.

B3

Reaction path B1 and B2 usually lead to the following intermediates IV or their related stereo isomers:

IV-1

IV-2

IV-3

IV-4 depending on the nature of the base.

Usually alkaline or earth metal alcoholates are used as base.

If the synthesis path B1 is followed, in formula IV E and the variables n, m, R$^6$ shall have the meaning: E=S, n=1, m=1 and R$^6$ has the meaning as specified above and if synthesis path B2 is followed $E_nR_m^6$ shall mean H and in either case the variable R$^3$ in formula IV has the meaning as defined above and G has the meaning as defined in IIb and Y has the meaning as defined in III b above.

For $E_nR_m^6$=—$SR^6$ and Y=—CN, —C(O)NH$_2$ the compounds shall be denoted as IV-1a, IV-2a, IV-3a, IV-4a and for $E_nR_m^6$=—H and Y=—CN, —C(O)NH$_2$ the compounds shall be denoted IV-1b, IV-2b, IV-3b, IV-4b.

For $E_nR_m^6$=—$SR^6$ and Y=—C(O)OR$^7$ the compounds shall be denoted as IV-1c, IV-2c, IV-3c, IV-4c.

For $E_nR_m^6$=—H and Y=—C(O)NH$_2$ the compounds shall be denoted as IV-1d, IV-2d, IV-3d, IV-4d.

Usually the intermediates IV are present in a mixture. From this mixture intermediates can be isolated e.g. by distillation or chromatography and characterized.

However it is not necessary to work up the mixture of IV yielded from path B1 and B2

B4

A certain group of this mixture as described below may be treated by the following three different ways which are generally known, and which lead to substituted pyridines as described below:

B 4-1 Bronsted Acid Catalysed Cyclization

Compounds and mixtures of formula IV-1 to IV-4 can be reacted with Bronsted-acids with or without an organic solvent. Temperatures between −30° C. and 150° C. can be used. The acid can be used between catalytic amounts and large excesses.

B 4-2 Zeolite Catalysed Cyclization

Compounds and mixtures of formula IV-1 to IV-4 can be reacted with alcohols and in case of Y=CN at high temperatures—normally between 150° C. and 300° C., under Lewis acid conditions on the surface of zeolite catalysts. The reaction can be performed as batch reaction (e.g. in an autoclave) or in a continuous manner (e.g. in a tube type reactor with the alcohol as carrier gas and reactant). Reaction can yield to isomers of 2-alcoxypyridines (formally product of a Pinner reaction) as well as to 2-hydroxypyridines. In the case of Y=C(O)OR1 it is necessary to do the reaction under an NH$_3$-enriched atmosphere in order to introduce the nitrogen atom in the pyridine ring.

B 4-3 Base, eg Ammonium Catalysed Cyclization

Compounds and mixtures of formula IV-1 to IV-4 can be reacted with ammonia or salts of ammonia under high temperature between 100° C. and 200° C. Reactions can be carried out with or without an inert solvent.

In all cases products can be isolated by extractive workup after hydrolysis with water. They can be purified by crystallization or, in certain cases, by distillation.

B 4-1 and B 4-3 lead usually to a) compounds I a-1 and I a-2 if the mixture containing IV-1a, IV-2a, IV-3a or IV-4a is used as starting material and b) compounds I a-3 and I a-4 if the mixture containing IV-1b, IV-2b, IV-3b or IV-4b is used as starting material.

B 4-2 leads usually a) to compounds I a-5

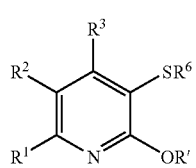

(Ia-5)

in which the variables have the above defined meaning, preferably $R^1=R^2=H$, $R^3$=—$CF_3$,. $R^6$=Me, R'=methyl, ethyl if the mixture containing IV-1a, IV-2a, IV-3a or IV-4a is used as starting material and b) to compounds Ia-6

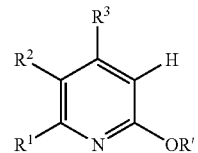

(Ia-6)

in which the variables have the above defined meaning, preferably R1=R2=H, R3=—CF3, R'=methyl, if the mixture containing IV-1b, IV-2b, IV-3b or IV-4b is used as starting material and if the used solvent is R'OH (R' having the meaning as defined above, preferably methyl).

B4-3a is a variation of B4-3. This base induced cyclization can be conducted in ammonia, preferably liquid ammonia, as solvent under usual conditions.

B 4-3a leads usually to compounds I a-1 or I a-2 if the mixture containing IV 1-c,a, IV-2c,a, IV 3-c,a, IV-4c,a is used as starting material and B 4-3a leads usually to the compounds I a-3 or I a-4 if the mixture containing IV-1b,d, IV-2b,d, IV-3b,d or IV-4b,d is used as starting material.

A suitable procedure to conduct the process of the instant invention is the following:

The Wittig Reagent or Horner Reagent is synthesized and—normally after isolation and purification is reacted with the α-β-unsaturated carbonyl compound (cf. path A2 or B2).

Usually the phosphorus organic compounds of type III are isolated and than further reacted with the α-β unsaturated carbonyl compound. This leads depending on the substitution of the α-β unsaturated carbonyl compound directly to the pyridine derivative (in case of 4-amino substituted α-β unsaturated carbonyl compound) or to the intermediates of formula IV (in case of 4-leaving group substituted α-β unsaturated carbonyl compound) which intermediates may than be cyclized.

Those intermediates preferably may be isolated and cyclisized by the above-mentioned reactions, or may be without isolation cyclized by the above mentioned cyclization reactions.

The process of the instant invention can be used in the synthesis of agrochemicals or pharmaceuticals e.g. agrochemicals as described in WO 02/36595 A2 (DOW Agr-Sciences LLC) or U.S. Pat. No. 5,571,775 (DOW Elanco) or Research Disclosure July 2002, 1230-1231 which are expressly incorporated by reference herein.

For example compound

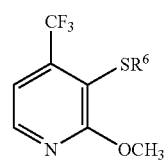

($R^6$=methyl) may be oxidized and chlorinated by usual methods leading to

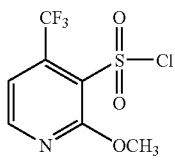

which then may be reacted in a known manner with 2-amino-[1,2,4]triazolopyrimidine or its derivatives, which derivatives are substituted on the six membered ring, preferably substituted on the six membered ring with $C_{1-20}$-alkyl (branched or straight chain or cyclic); $C_{6-20}$-aryl—which each of those may be substituted with one or more of the following groups: F, Cl, Br, I, $C_{1-20}$-alkoxy, $C_{6-20}$-aryloxy, non substituted or preferably substituted amino-; F; Cl; Br; I; $C_{1-20}$-alkoxy; $C_{6-20}$-aryloxy; very preferably substituted with the before mentioned groups on the 5,7 positions on the six membered ring, for example

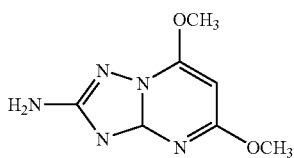

which yields usually the respective sulfonamide compound, for example

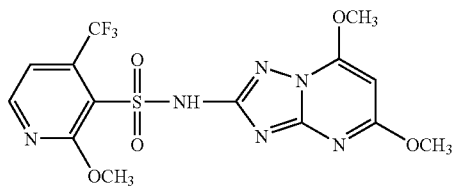

The process of the instant invention leads regioselectively to valuable pyridine derivatives which may be used as valuable compounds for the preparation of pharmaceuticals, agrochemicals, in particular sulfonamide type herbicides, or other chemicals.

EXAMPLES

The following examples were conducted under standard conditions of preparative organic chemistry.

Trifluoromethyl-diethoxypentene Acid Ethyl Ester (Mixture of Isomers)

17.1 g (0.1 mol) 4-ethoxy-1,1,1-trifluoro-but-3-en-2-one was dissolved in 200 ml dry ethanol. 22.8 g (0.1 mol) phosphono acetic acid triethyl ester was added within 10 min. at 10-13° C. 9.5 g (o.133 mol) Sodium ethoxide was metered in within 25 min. at 0-2° C. The mixture was concentrated under vacuum (50-1 mbar) at 40-60° C. 200 ml Dichloromethane was added. The organic phase was extracted twice with each 85 ml water. The solvent was evaporated at 40-70° C. (100-15 mbar).

Yield: ca. 67% in respect to the 4-ethoxy-1,1,1-trifluoro-but-3-en-2-one 2-hydroxy-4-(trifluoromethyl)pyridine 103.5 g (0.35 mol) 3-trifluoromethyl-diethoxypentene acid ethyl ester (mixture of isomers, amount based on GC area-%) and 51.3 g (0.665 mol) ammonium acetate were heated to 150-155° C. over 8 h. A mixture of ethanol, acetic acid and acetic acid ethyl ester (ca. 60 g) was distilled off through a small column (20 cm, filled with 3 mm rings) during this heating period. The sump (79.8 g) can directly be transferred to the next step (yield has been determined only after final methoxylation step).

Yield: 67.6% in respect to 3-trifluoromethyl-5-diethoxypentene acid ethyl ester

Phosphonoacetonitrile Diethyl Ester 677.5 g (4.0 mol) triethyl phosphite were heated to 150° C. 152.4 g (2.0 mol) chloroacetonitrile were added at 150° C. over a period of 2 h (offgas chloroethane). The mixture was held for 2 more hours at 150° C. (until gas evolvement is finished). The mixture was distilled over a small Vigreux column (10 cm). The last fraction with bp 110-139° C. at 1 mbar contained the product.

Yield: 99% in respect to chloroacetonitrile (based on GC area-%)

2-Methylthio-phosphonoacetonitrile Diethyl Ester 25.7 g (1.05 mol) sodium hydride was added to 500 ml dry THF under nitrogen. 88.9 g (0.5 mol) phosphonoacetonitrile diethyl ester was metered in within 30 min. at 25-40° C. The mixture was stirred for 30 more min. at 30° C. 94 g (1.0 mol) dimethyldisulfide was added within 30 min. at 25° C. and the reaction mixture stirred over night The mixture was added to 400 ml Cl (10%) within 15 min at 25° C. and was extracted twice with each 250 ml MTBE. MTBE was evaporated under vacuum (2 mbar, 50° C.).

Yield: ca. 87%

5,5-Diethoxy-2-thiomethyl-3-trifluoromethyl-pent-2-ene-nitrile 5 g (0.13 mol) lithium methoxide was added to 20 ml dry methanol. A mixture of 17 g (0.101 mol) 4-ethoxy-1,1,1-trifluoro-but-3-en-2-one and 24.2 g (0.1 mol) 2-methylthio-phosphono acetonitrile diethyl ester in 200 ml methanol was added at 20-35° C. For reaction completion the mixture was stirred over night. The solvent was evaporated at 50° C. under vacuum. 180 ml Ethyl acetate and 150 ml Water were added and the phases mixed. The organic phase was separated and the aqueous phase extracted twice with each 100 ml ethyl acetate. The combined organic layers were dried over sodium sulfate and afterwards concentrated under vacuum.

Yield: ca. 74% (mixture of E/Z-isomers) in respect to the 4-ethoxy-1,1,1-trifluoro-but-3-en-2-one.

2-hydroxy-3-thiomethyl-4-(trifluoromethyl)pyridine 62.0 g (0.22 mol) 5,5-Diethoxy-2-methylsulfanyl-3-trifluoromethyl-pent-2-enenitrile was dissolved in a mixture of 157.0 g Ethanol and 200.0 g 10% sulphuric acid. The reaction mixture was heated up to reflux at 70° C. for 5 hours. After complete reaction the ethanol was removed under vacuum (120-20 mbar) at 40° C. During distillation the product precipitated as light yellow crystals. The crude product was washed with 9.0 g ethyl acetate. From the washing liquor additional product could be isolated by crystallisation.

Yield: 35.4 g corresponding to 77%

2-hydroxy-4-(trifluoromethyl)-pyridine 5 g (0.036 mol) 4-amino-1-trifluoromethylbut-3-en-2-one was dissolved in 50 ml methanol. To the mixture were metered during 10 minutes 8 g (0.036 mol) triethylphosphonoacetate in 10 ml methanol as well as 7.7 g of a 30% sodium methoxide solution in methanol. The reaction mixture was stirred over night and after removing the solvent in vacuum the crude product was isolated after hydrolysis with water and extraction at pH 4.

Yield: 1.5 g 25%

2-hydroxy-4-(trifluoromethyl)-pyridine 5 g (0.036 mol) trifluoromethyldiethoxypentene acid ethyl ester (mixture of isomers) were dissolved in 40 g THF. The solution was metered during 150 minutes into a 250° C. hot tube reactor, which was filled with a boron doped zeolite catalyst. As carrier gas a mixture of 100 l $N_2$/h and as reactant 50 l $NH_3$/h were pumped through the reactor. The outcoming gas was cooled and quenched into THF yielding to a mixture auf 90% of the desired product as well as 5% 2-ethoxy-4-(trifluoromethyl)pyridine.

2-ethoxy-4-(trifluoromethyl)-pyridine 5 g (0.036 mol) trifluoromethyldiethoxypentene acid ethyl ester (mixture of isomers) were dissolved in 80 g ethanol. The solution was metered during 150 minutes into a 250° C. hot tube reactor, which was filled with a boron doped zeolite catalyst. As carrier gas a mixture of 100 l $N_2$/h and as reactant 100 l $NH_3$/h were pumped through the reactor. The outcoming gas was cooled and quenched into THF yielding to a mixture containing 70% 2-ethoxy-4-(trifluoromethyl)pyridine.

2-hydroxy-4-(trifluoromethyl)-pyridine 21.4 g (0.075 mol) trifluoromethyldiethoxypentene acid ethyl ester (mixture of isomers) and 2 g of a boron doped zeolite catalyst were placed in an autoclave and 12.75 g of ammonia (0.75 mol) were pressed. The mixture was stirred at 230° C. for 30 minutes and after cooling the residue contained 74% of the desired product.

2-hydroxy-4-(trifluoromethyl)-pyridine 21.4 g (0.075 mol) trifluoromethyldiethoxypentene acid ethyl ester (mixture of isomers) and 2 g of a boron doped zeolite catalyst were placed in an autoclave and 6.4 g of liquid ammonia (0.38 mol) were dosed. The mixture was stirred at 230° C. for 30 minutes and after cooling the residue was dissolved in methylene chloride, washed and after distillation of the solvent 9.5 g (99% GC) of the crude product was isolated.

Yield: 74%

2-hydroxy-3-thiomethyl-4-(trifluoromethyl)-pyridine 5 g (0.018 mol) 5,5-diethoxy-2-thiomethyl-3-trifluoromethyl-pent-2-ene-nitrile (mixture of isomers), 2 g of a boron doped zeolite catalyst and 21 g methanol were was stirred at 230° C. for 60 minutes and after cooling the residue contained 39% of the desired product, 17% of 2-methoxy-3-thiomethyl-4-(trifluoromethyl)-pyridine and 2% of 2-amino-3-thiomethyl-4-(trifluoromethyl)-pyridine.

2-hydroxy-3-thiomethyl-4-(trifluoromethyl)-pyridine 5 g (0.018 mol) 5,5-diethoxy-2-thiomethyl-3-trifluoromethyl-pent-2-ene-nitrile (mixture of isomers and 2.7 g ammonium acetate were stirred at 150° C. in a flask for 12 hours. After cooling the residue contained 20% of the desired product, and 37% of 2-amino-3-thiomethyl-4-(trifluoromethyl)-pyridine.

5,5-Diethoxy-2-thiomethyl-3-trifluoromethyl-pent-2-ene-nitrile

To a solution of 30 g (0.13 mol) 2-methylthio-phosphono acetonitrile diethyl ester and 22.6 g (0.13 mol) 4-ethoxy-1,1,1-trifluoro-but-3-en-2-one in 100 ml dry ethanol was metered 59.9 g of a 20% sodium ethoxide solution within 30 minutes. The reaction mixture was stirred for 2 hours at 70° C. After cooling the solvent was removed under vacuum. 100 ml toluene and 150 ml Water are added and the phases mixed. The organic phase is separated and the aqueous phase extracted twice with each 100 ml toluene. The combined organic layers are dried over sodium sulfate and afterwards concentrated under vacuum.

Yield: ca. 40%

5,5-Diethoxy-2-thiomethyl-3-trifluoromethyl-pent-2-ene-nitrile

To a solution of 50 g (0.22 mol) 2-methylthio-phosphono acetonitrile diethyl ester and 37.7 g (0.22 mol) 4-ethoxy-1,1,1-trifluoro-but-3-en-2-one in 100 g dry ethanol was metered 98.6 g of a 20% sodium ethoxide solution within 30 minutes. The reaction mixture was stirred for 3 hours under reflux. After cooling the solvent was removed under vacuum. 200 ml toluene and 100 ml Water are added and the phases mixed. The organic phase is separated and the aqueous phase extracted twice with each 100 ml toluene. The combined organic layers are dried over sodium sulfate and afterwards concentrated under vacuum.

Yield: ca. 52%

5,5-Diethoxy-2-thiomethyl-3-trifluoromethyl-pent-2-ene-nitrile

To a solution of 9 g (0.04 mol) 2-methylthio-phosphono acetonitrile diethyl ester and 12 g (0.071 mol) 4-ethoxy-1,1,1-trifluoro-but-3-en-2-one in 100 ml dry ethanol was metered a solution of 1.8 g (0.075 mol) lithium hydroxide in 50 ml of ethanol within 30 minutes. The reaction mixture was stirred for 5 hours under reflux. After cooling the solvent was removed under vacuum. 100 ml toluene and 50 ml Water were added and the phases mixed. The organic phase was separated and the aqueous phase extracted twice with each 100 ml toluene. The combined organic layers were dried over sodium sulfate and afterwards concentrated under vacuum.

Yield: ca. 70%

5,5-Diethoxy-2-thiomethyl-3-trifluoromethyl-pent-2-ene-nitrile

To a solution of 2.8 g (0.054 mol) of an 1 M lithium ethoxide solution in ethanol was metered at 50° C. a solution of 10 g (0.045 mol) 2-methylthio-phosphono acetonitrile diethyl ester and 7.5 g (0.13 mol) 4-ethoxy-1,1,1-trifluoro-but-3-en-2-one in 100 ml dry ethanol. The reaction mixture was stirred for 2 hours at 60° C. 200 ml ethyl acetate were added and the organic phase was washed twice with 100 g of water. The organic layer was dried over sodium sulfate and afterwards concentrated under vacuum.

Yield: ca. 79%

5,5-Dimethoxy-2-thiomethyl-3-trifluoromethyl-pent-2-ene-nitrile

To a mixture of 5 g (0.63 mol) lithium hydride in 100 ml dry THF was metered a solution of 95 g (0.43 mol) 2-methylthio-phosphono acetonitrile diethyl ester and 72 g (0.43 mol) 4-ethoxy-1,1,1-trifluoro-but-3-en-2-one in 800 ml dry methanol. During addition the temperature raised to 40° C. Afterwards the reaction mixture was stirred for additional 2 hours at 25° C. The solvent was removed under vacuum. 250 ml ethyl acetate were added and the organic phase was washed three times with 100 g of water. The organic layer was dried over sodium sulfate and afterwards concentrated under vacuum.

Yield: ca. 85%

The invention claimed is:

1. A process for the preparation of substituted pyridine derivatives of formula (I)

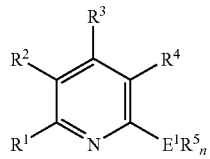

(I)

wherein
R$^1$ and R$^2$ independently represent H C$_{1-20}$-alkyl (branched or straight chain or cyclic) or C$_{6-20}$-aryl, each of which alkyl and aryl groups may be substituted with one or more of the following groups: F, Cl, Br, I, C$_{1-20}$-alkoxy or C$_{6-20}$-aryloxy each of which alkoxy or aryloxy groups may be substituted with amino, F, Cl, Br or I;
R$^3$ represents C$_{1-20}$-alkyl (branched or straight chain or cyclic) or C$_{6-20}$-aryl, each of which alkyl and aryl groups may be substituted with one or more of the following groups: F, Cl, Br, I, C$_{1-20}$-alkoxy or C$_{6-20}$-aryloxy, each of which alkoxy or aryloxy groups may be substituted with amino, F, Cl, Br, or I;
R$^4$ represents E$_n$R$^6_m$ in which
if n=m=1, then E represents S and R$^6$ represents C$_{1-20}$-alkyl (branched or straight chain or cyclic) or C$_{6-20}$-aryl, each of which may be substituted with one or more of the following groups: F, Cl, Br, I, C$_{1-20}$-alkoxy or C$_{6-20}$-aryloxy, each of which alkoxy or aryloxy groups may be substituted with amino, F, Cl, Br or I;
if n=0 and m=1 than R$^6$=H, C$_{1-20}$-alkyl (branched or straight chain or cyclic) or C$_{6-20}$-aryl, each of which alkyl and aryl groups may be substituted with one or more of the following groups: F, Cl, Br, I, C$_{1-20}$-alkoxy or C$_{6-20}$-aryloxy, each of which alkoxy or aryloxy groups may be substituted with amino, F, Cl, Br or I;
E$^1$ represents O or N;
R$^5$ represents H; and
n=1 when E$^1$ represents O and n=2 when E$^1$=N which comprises:
i) reacting an α-β-unsaturated carbonyl compound of formula (II)

$$R^3—C(O)—C(R^1)=C(R^2)-G \qquad (II)$$

wherein
R$^1$, R$^2$ and R$^3$ are as previously defined; and
G represents —NH$_2$ or a leaving group
with a Wittig reagent or Horner-Wadsworth-Emmons reagent of formula (III)

(IIIa1)

(IIIa2)

wherein
(P) represents P(Ar)$_3$, in which Ar represents a substituted or preferably unsubstituted C$_{6-20}$ aryl, R' independently represents C$_{1-20}$ alkyl (branched or straight or cyclic) or C$_{6-20}$ aryl;
M represents an alkaline metal (Li, Na, K, Rb or Cs);
E$_n$R$^6_m$ is as previously defined;
Y represents —CN; —C(O)NH$_2$; —C(O)OR$^7$ in which R$^7$ is as defined for R$^3$ above in the presence of a base to provide a mixture of intermediates; and
ii) cyclizing the mixture of intermediates to the substituted pyridine of formula (I) by:
a) catalysis with acid, catalysis with zeolites or catalysis with base when Y represents —CN or C(O)NH$_2$, G represents a leaving group and the base is an alcoholate; or
b) catalysis with base in the presence of ammonia when Y represents —C(O)—OR$^7$, G represents a leaving group and the base is an alcoholate.

2. The process according to claim 1, wherein R$^1$ and R$^2$ both represent H and R$^3$ represents an electron withdrawing group.

3. The process according to claim 1, wherein R$^1$ and R$^2$ both represent H and R$^3$ represents a partially or fully fluorinated C$_{1-6}$-alkyl group.

4. The process according to claims 1, wherein R$^3$ represents —CF$_3$.

* * * * *